(12) United States Patent  
Mikami

(10) Patent No.: US 9,581,497 B2  
(45) Date of Patent: Feb. 28, 2017

(54) CARS MICROSCOPE

(71) Applicant: Hitachi, Ltd., Chiyoda-ku, Tokyo (JP)

(72) Inventor: Hideharu Mikami, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/435,439

(22) PCT Filed: Oct. 19, 2012

(86) PCT No.: PCT/JP2012/077030  
§ 371 (c)(1),  
(2) Date: Apr. 13, 2015

(87) PCT Pub. No.: WO2014/061147  
PCT Pub. Date: Apr. 24, 2014

(65) Prior Publication Data  
US 2015/0276483 A1 Oct. 1, 2015

(51) Int. Cl.  
*G01B 9/02* (2006.01)  
*G01J 3/44* (2006.01)  
(Continued)

(52) U.S. Cl.  
CPC ............... *G01J 3/44* (2013.01); *G01J 3/0205* (2013.01); *G01J 3/10* (2013.01); *G01N 21/65* (2013.01);  
(Continued)

(58) Field of Classification Search  
CPC .......... G01J 3/10; G01J 3/45; G01J 3/02; G01J 3/04; G01J 2003/45; G01N 21/65; G01N 21/00; G01N 21/17; G01N 21/45; G01N 2021/653; G01N 2201/06113; G02B 21/0004; G02B 21/002; G02B 21/06; G02B 21/16; G01B 9/02029; G01B 9/02065; G01B 9/0207; G01B 9/0209; G01B 9/02092; G01B 2290/45  
(Continued)

(56) References Cited

U.S. PATENT DOCUMENTS

2005/0280827 A1 12/2005 Potma et al.  
2006/0238745 A1* 10/2006 Hashimoto ............... G01J 3/44  
356/73

(Continued)

FOREIGN PATENT DOCUMENTS

JP 2004-534232 A 11/2004  
JP 2010-139327 A 6/2010  
(Continued)

OTHER PUBLICATIONS

Denk, Winfried, et al., "Two-Photon Laser Scanning Fluorescence Microscopy", Science, vol. 248, Issue 4951, pp. 73-76 (1990).  
(Continued)

*Primary Examiner* — Tarifur Chowdhury  
*Assistant Examiner* — Jonathon Cook  
(74) *Attorney, Agent, or Firm* — Miles & Stockbridge P.C.

(57) ABSTRACT

A microscope includes: a first light dividing part that divides a light flux of light from a light source into a first pump light flux and a second pump light flux; a Stokes light source that receives the second pump light flux as an input and outputs a Stokes light flux; a multiplexing part that multiplexes the first pump light flux and the Stokes light flux to generate a multiplexed light flux; a first light-collecting part that collects the multiplexed light flux in a sample; a first detector that detects CARS light generated from the sample, the CARS light having a wavelength different from the multiplexed light flux; a second light dividing part that lets at least one of the second pump light flux and the Stokes light flux (Continued)

branch partially as a reference light flux; a second multiplexing part that multiplexes a light flux from the sample and the reference light flux to generate interfering light; and a second detector that detects the interfering light.

17 Claims, 12 Drawing Sheets

(51) Int. Cl.
| | | |
|---|---|---|
| *G01N 21/65* | (2006.01) | |
| *G02B 21/16* | (2006.01) | |
| *G02B 21/00* | (2006.01) | |
| *G02B 21/06* | (2006.01) | |
| *G01J 3/02* | (2006.01) | |
| *G01J 3/10* | (2006.01) | |

(52) U.S. Cl.
CPC ......... *G02B 21/002* (2013.01); *G02B 21/0004* (2013.01); *G02B 21/06* (2013.01); *G02B 21/16* (2013.01); *G01N 2021/653* (2013.01); *G01N 2201/06113* (2013.01)

(58) Field of Classification Search
USPC .......................................................... 356/484
See application file for complete search history.

(56) References Cited

U.S. PATENT DOCUMENTS

| | | | | |
|---|---|---|---|---|
| 2008/0059135 | A1* | 3/2008 | Murugkar | G01J 3/4338 703/11 |
| 2010/0309465 | A1* | 12/2010 | Liu | G01J 3/44 356/301 |
| 2012/0050720 | A1* | 3/2012 | Kim | G01J 3/10 356/51 |

FOREIGN PATENT DOCUMENTS

| | | |
|---|---|---|
| JP | 2012-018122 A | 1/2012 |
| WO | WO 03/004983 A1 | 1/2003 |

OTHER PUBLICATIONS

Campagnola, Paul J., et al., "Second-harmonic imaging microscopy for visualizing biomolecular arrays in cells, tissues and organisms", Nature Biotechnology 21, pp. 1356-1360 (2003).
Okuno, M. et al., "Quantitative Cars Molecular finger printing of living Cells", Angewandte Chemie International Edition 49, 6773-6777 (2010).
Saar, Brian G., et al., "Video-Rate Molecular Imaging in Vivo with Stimulated Raman Scattering", Science, vol. 330, pp. 1368 (2010).
Day, J.P.R., et al., "Quantitative Coherent Anti-Stokes Scattering (CARS) Microscopy", J. Phys. Chem. B, vol. 115, 7713-7725 (2011).
Wojtkowski, M. et al., "Full range complex spectral optical coherence tomography technique in eye imaging", Optics Letters, vol. 27, Issue 16, pp. 1415-1417 (2002).
Begin, S. et al., "Coherent anti-Stokes Raman scattering hyperspectral tissue imaging with a wavelength-swept system", Biomedical Optics Express, vol. 2, Issue 5, pp. 1296-1306 (2011).
Yasuno, Y. et al., "Three-dimensional and high-speed swept-source optical coherence tomography for in vivo investigation of human anterior eye segments", Optics Express, vol. 13, Issue 26, pp. 10652-10664 (2005).
Bredfeldt, J. S., et al., "Molecularly sensitive optical coherence tomography", Optics Letters, vol. 30, No. 5, pp. 495-497, Mar. 1, 2005.
Sarunic M. V., et al., "Spectral domain second-harmonic optical coherence tomography", Optics Letters, vol. 30, No. 18, pp. 2391-2393, Sep. 15, 2005.
Vinegoni, C., et al., "Nonlinear optical contrast enhancement for optical coherence tomography", Optics Express, vol. 12, No. 2, pp. 331-341, Jan. 26, 2004.
Labruyere, A., et al., "Compact supercontinuum sources and their biomedical applications", Optical Fiber Technology, vol. 18, No. 5, pp. 375-378, Sep. 2012.
Mitsuo Gomi, et al., "A Remote Laser-Probing System for Combustion Measurements", Technical Report of National Aerospace Laboratory, No. 979, pp. 1-18, Jun. 1988.
Supplementary European Search Report dated Apr. 26, 2016 for corresponding EP Application No. 12886672.0.
Hoffmann et al. "Combined OCT and CARS using a single ultrashort pulse Ti:Sapphire laser", Multimodal Biomedical Imaging VI, SPIE, vol. 7892, No. 1, pp. 1-8 (Feb. 10, 2011).
Lu et al., "Interferometric polarization coherent anti-Stokes Raman scattering (IP-CARS) microscopy", Optics Letter, Optical Society of America, vol. 33, No. 6, pp. 602-604 (Mar. 15, 2008).
Potma et al., "Heterodyne coherent anti-Stokes Raman scattering (CARS) Imaging", Optics Letters, Optical Society of American, vol. 31, No. 2, pp. 241-243 (Jan. 15, 2006).

* cited by examiner (a)      (b)      (c)

CARS MICROSCOPE

TECHNICAL FIELD

The present invention relates to high-performance optical microscopes.

BACKGROUND ART

Optical microscopes are, needless to say, observation tools that are indispensable in the field of natural science, engineering and industries. Especially a high-performance microscope including a laser as an illumination light source has been recently essential for the development of advanced technology. A typical example of such a microscope is a fluorescence confocal microscope, which is widely used in combination with fluorescent reagent in the field of medicine and biology as means to observe the spatial distribution of a specific substance in a biological sample. Coupled with a sophisticated short-pulse laser light source becoming available in recent years, techniques for a non-linear optical microscope based on non-linear optical effects have been developed, and needs therefor in the field of medicine and biology have been grown noticeably. Known examples of such a non-linear optical microscope (or non-linear microscope) include a two-photon fluorescence microscope (Non Patent Literature 1), a SHG microscope (Non Patent Literature 2), a coherent anti-stokes Raman scattering (CARS) microscope (Non Patent Literature 3), and a stimulated Raman scattering (SRS) microscope (Non Patent Literature 4). For instance, a two-photon fluorescence microscope allows a small wavelength band less absorbing the sample to be selected as laser light to be applied to the sample, and so imaging is enabled at a deep part as compared with a conventional fluorescence confocal microscope. A SHG microscope is to observe second harmonics from the sample, which can detect the fiber structure of collagen or the like and a specific structure such as cell membrane selectively. A CARS microscope is configured to irradiate a sample with two types of lights including pump light and Stokes light, and to observe anti-Stokes light generated as a result of the resonance of the frequency difference between these lights with the natural vibration of the molecules of the sample. Based on the distribution of wavelength and intensity of the anti-Stokes light, the spatial distribution of a specific substance in the sample can be observed, and so this technique has attracted attention as a labeling-free and non-invasive microscope as a substitute of a fluorescence microscope. A SRS microscope is configured to irradiate a sample with pump light and Stokes light similarly to the CARS microscope, and to observe the natural vibration of the substance in the form of a change in intensity of these two types of lights, which also is a non-invasive microscope like the CARS microscope. In this way, a non-linear optical microscope can provide various sophisticated observation means, which cannot be implemented with conventional microscopes.

The following describes the operating principle of the CARS microscope. CARS is the emission of light due to third-order polarization, and in order to generate CARS, pump light, Stokes light and probe light are required. Typically in order to reduce the light sources in number, the pump light doubles as the probe light. In this case, induced third-order polarization will be represented by [Math. 1]:

$$P_{AS}^{(3)}(\omega_{AS}) = |\chi_r^{(3)}(\omega_{AS}) + \chi_{nr}^{(3)}|E_P^2(\omega_P)E^*_S(\omega_S) \quad [\text{Math. 1}]$$

In this expression, $\chi r^{(3)}(\omega_{AS})$ is the resonant term of the molecule vibrations of third-order electric susceptibility, and $\chi nr^{(3)}$ is the non-resonant term. EP represents the electric field of the pump light and the probe light, and ES represents the electric field of the Stokes light. The non-resonant term does not have frequency-dependency. Asterisk attached to the shoulder of ES in [Math. 1] denotes a complex conjugate. Then the intensity of CARS light is represented as follows:

$$I_{CARS}(\omega_{AS}) \propto |P_{AS}^{(3)}(\omega_{AS})|^2 \quad [\text{Math. 2}]$$

Referring to the energy level diagram (FIG. 14) of molecules, the following describes the mechanism to generate CARS light. This drawing illustrates the process for the resonant term. Numeral 1401 denotes the ground state of molecule vibrations, and 1402 denotes the excitation state of vibrations. Pump light at a frequency $\omega_P$ and Stokes light at a frequency $\omega_S$ are applied simultaneously. At this time, molecules are excited to some excitation level of vibrations in 1402 via an intermediate state 1403. When the molecules in such an excitation state are irradiated with the probe light at a frequency $\omega_P$, then the molecules return to the ground state of vibrations while emitting CARS light at a frequency of $\omega_{AS}$ via an intermediate state 1404. The frequency of the CARS light at this time is represented as $\omega_{AS} = 2\cdot\omega_P - \omega_S$.

As is evident from FIG. 14, this resonant CARS light is generated only when the difference in frequency $\omega_P - \omega_S$ between the pump light and the Stokes light is equal to a certain vibration excitation state of the sample observed (Note here that Planck units are used here, where the Planck constant is 1). That is, when a broadband light source is used for the Stokes light, then the CARS light generated also becomes broadband light, and has a spectrum having a sharp peak at the wavelength corresponding to the vibration excitation state. This spectrum is called Raman spectrum, which reflects the spatial distribution of vibration excitation state of the molecules in the sample, and so can be used for identification of the molecular species.

FIG. 15 illustrates one process relating to the non-resonant term in Math. 1. The Stokes light has the frequency that is not in the vibration excitation state, and the process occurs via an intermediate state 1405. When the pump light at the frequency $\omega_P$ and probe light at a frequency $\omega'_P$ are applied simultaneously, then the intermediate state 1405 involving electrons or the like is excited, and when Stokes light at a frequency of $\omega'_P$ is further applied, non-resonant CARS light at a frequency of $\omega_{AS}$ is generated via an intermediate state 1406. This non-resonant CARS light is generated irrespective of the vibration excitation state, and so when broadband Stokes light is used, broadband non-resonant CARS light is generated, whose intensity does not have frequency-dependency. These resonant CARS light and non-resonant CARS light are mutually coherent, and so interference occurs therebetween. Since the spectrum of the resonant CARS light, i.e., the Raman spectrum, actually is required to identify the molecular species in the sample, signal processing has to be performed to acquire the Raman spectrum from the CARS light spectra acquired. Some methods are known for such signal processing (see Non Patent Literature 5), and for example, in the method of maximum entropy that is to recover a phase spectrum from the intensity spectrum, mathematical operation is performed to find the complex component of the resonant term.

The pump light, the Stokes light and the CARS light have a relationship for frequency as in FIG. 16. When the pump light at a predetermined frequency and the Stokes light in a frequency area smaller than that are incident on the sample, then CARS light is generated in a frequency area that is larger than the pump light.

The CARS microscope is configured to measure the thus found Raman spectrum a plurality of times while changing the focusing position of the pump light and the Stokes light, and acquire an image of the spatial distribution for each molecular species as a result.

CITATION LIST

Non Patent Literatures

Non Patent Literature 1: W. Denk et al., "Two-Photon Laser Scanning Fluorescence Microscopy", Science, Volume 248, Issue 4951, pp. 73-76 (1990)
Non Patent Literature 2: P. J. Campagnola et al., "Second-harmonic imaging microscopy for visualizing biomolecular arrays in cells, tissues and organisms", Nature Biotechnology 21, 1356-1360 (2003)
Non Patent Literature 3: M. Okuno et al., "Quantitative CARS Molecular finger printing of living Cells", Angewandte Chemie International Edition 49, 6773-6777 (2010)
Non Patent Literature 4: B. G. Saar et al., "Video-Rate Molecular Imaging in Vivo with Stimulated Raman Scattering", Science Vol. 330 1368 (2010)
Non Patent Literature 5: J. P. R. Day, K. F. Domke, G. Rago, H. Kano, H. Hamaguchi, E. M. Vartiainen, and M. Bonn, "Quantitative Coherent Anti-Stokes Scattering (CARS) Microscopy", J. Phys. Chem. B, Vol. 115, 7713-7725 (2011)

SUMMARY OF INVENTION

Technical Problem

The above-mentioned fluorescence confocal microscope and non-linear optical microscope are common in the feature of visualizing the spatial distribution of the substance species of the sample and the spatial distribution of a specific structure of the sample. These microscopes, however, cannot acquire the optical characteristics, i.e., basic information such as the index of refraction and the transmittance of the sample. For observation of a biological sample such as cells, not only information on the substance spatial distribution that can be acquired by a non-linear optical microscope or a fluorescence confocal microscope but also information on the index of refraction and the transmittance are required in some cases for detailed analysis of the sample. To this end, in the case of such microscopy, a bright field microscope, a phase-contrast microscope or the like that has been used for a long time is used in combination accessorily. Such microscopy, however, cannot give quantitative spatial distribution of the index of refraction and the transmittance, which gives just accessory information to know the shape of the sample.

In view of these problems, the present invention aims to provide a microscope giving the spatial distribution of substance species and a specific structure of a sample as well as the quantitative spatial distribution of optical characteristics such as index of refraction and transmittance of the sample.

Solution to Problem

To fulfill the object of the present invention, the following means is used.

(1) A microscope includes: a light source such as a short-pulse laser light source; a first light dividing part such as a beam splitter that divides a light flux of output light from the light source into a first pump light flux and a second pump light flux; a Stokes light source such as a photonic crystal fiber that receives the second pump light flux as an input and outputs a Stokes light flux; a multiplexing part such as a dichroic mirror that multiplexes the first pump light flux and the Stokes light flux to generate a multiplexed light flux; a first light-collecting part such as an objective lens that collects the multiplexed light flux in a sample; a first detector such as a spectroscope that detects CARS light generated from the sample, the CARS light having a wavelength different from the multiplexed light flux; a second light-collecting part such as a spectroscope that guides the CARS light to the first detector; a second light dividing part such as a non-polarizing beam splitter that lets at least one of the first pump light flux and the Stokes light flux branch partially as a reference light flux; a second multiplexing part such as a non-polarizing beam splitter that multiplexes a light flux from the sample and the reference light flux to generate interfering light; and a second detector such as a spectroscope that detects the interfering light.

This configuration enables acquisition of quantitative spatial distribution of substance species in the sample through the detection of CARS light and acquisition of spatial distribution of index of refraction of the sample, and so more information can be acquired from the sample as compared with conventional microscopes.

(2) In (1), the Stokes light source is an optical parametric oscillator and the like that makes the wavelength of the Stokes light flux variable continuously.

This can eliminate dispersion of the wavelength at a detector that detects CARS light and a detector that detects interfering light, and so the detector can have a simple configuration.

(3) In (1), the Stokes light source is a photonic crystal fiber and the like that generates the Stokes light flux whose wavelength has a broader bandwidth than the second pump light flux.

This allows a detector that detects CARS light to acquire information on a plurality of wavelengths at the same time using a spectroscope, which can contribute to high-speed data acquisition.

(4) In (2) or (3), the reference light flux and the light flux from the sample each includes Stokes light.

This enables measurement of the spatial distribution of index of refraction in the optical axis of the sample collectively, which can contribute to high-speed data acquisition.

(5) In (4), the Stokes light flux has a light-flux diameter that is smaller than a light-flux diameter of pump light multiplexed by the multiplexing part.

This enables both of the generation of a CARS signal effectively and of the acquisition of spatial distribution of index of refraction of the sample in the optical axis direction in a broader range collectively.

(6) In (4), the CARS microscope further includes a light-flux varying part such as a phase modulator element that makes a light-flux diameter of the first Stokes light variable.

This enables all of the generation of a CARS signal effectively, of the generation of interfering light effectively and of the acquisition of spatial distribution of index of refraction of the sample in the optical axis direction in a broader range collectively.

(7) In (1), the CARS microscope further includes: a first polarized-light conversion part such as a $\lambda/4$ plate that makes polarized light of the reference light arbitrarily variable; and a second polarized-light conversion part such as a λ/4 plate that makes polarized light of the Stokes light arbitrarily variable;

This can measure not only the spatial distribution of index of refraction of the sample but also the spatial distribution of birefringence of the sample through the detection of the interfering light, whereby more information can be acquired from the sample.

(8) In (4), the CARS microscope includes one spectroscope as the first detector and the second detector.

This can reduce the number of components of a spectrometer that typically is in a large scale, which can contribute to a simplified microscope.

(9) In (1), the CARS microscope further includes: at least one of a third detector that detects SHG and a fourth detector that detects two-photon fluorescence, the SHG and the two-photon fluorescence being generated from the sample irradiated with a pump light flux.

This can acquire more information from the sample.

Advantageous Effects of Invention

An optical microscope can be provided, which can acquire more detailed information on a target to be observed than conventional microscopes.

DESCRIPTION OF EMBODIMENTS

Embodiment 1

Figure 1:
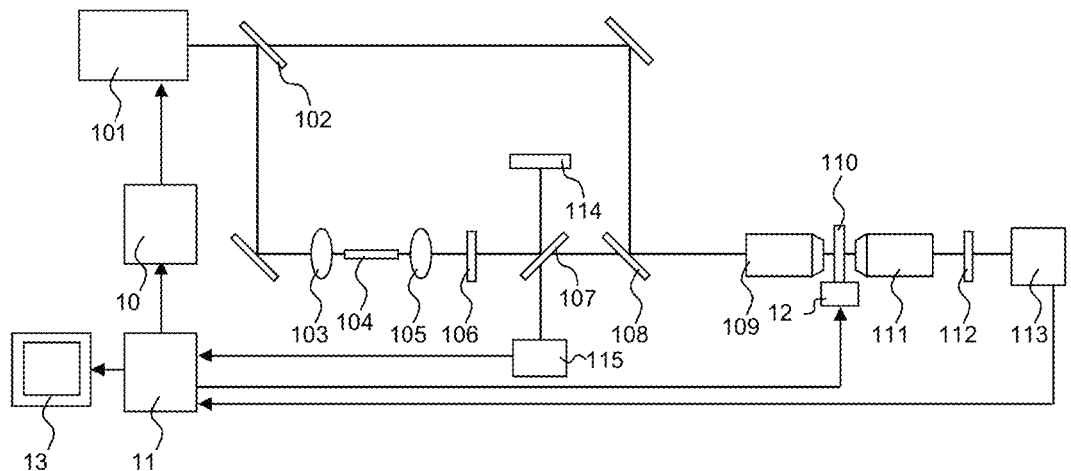
FIG. 1 illustrates a basic embodiment of the present invention.

FIG. 1 illustrates a basic embodiment of an optical microscope of the present invention. The following describes the operation thereof by way of the drawing.

Laser light emitted from a short-pulse laser light source 101 that is controlled in light-emission by a driver 10 receiving a command from a computer 11 is divided at a beam splitter 102 into two, including transmitted light as pump light and reflected light. The reflected light is coupled with a photonic crystal fiber 104 via a collecting lens 103, whereby broadband supercontinuum light is generated inside the fiber. The thus generated supercontinuum light is made parallel light via a collimate lens 105, passes through a long-pass filter 106, along which a component at the wavelength of the short-pulse laser light source and the wavelengths shorter than that are blocked, and is branched into transmitted light as Stokes light and reflected light as reference light at a non-polarizing beam splitter 107. Between them, the Stokes light is multiplexed with the pump light at a dichroic mirror 108. Herein the dichroic mirror 108 has the property of reflecting lights at the wavelength of the pump light and in the wavelength band shorter than that, and transmitting light in the wavelength band longer than the pump light. Then the pump light is reflected and the Stokes light is transmitted, resulting in multiplexing. This multiplexed light flux is collected at one point on a sample 110 via an objective lens 109, whereby CARS light is generated, which reflects the resonant vibrations of molecules present at the light-collecting position on the sample. The CARS light is then made a parallel light via a condenser lens 111, passes through a short-pass filter 112 that blocks the pump light and the Stokes light that are coaxial components, and then is incident on a spectroscope 113, where the spectrum is output as a detected signal. This detected signal undergoes predetermined signal processing to remove non-resonant background, and then a signal corresponding to a resonant spectrum (Raman spectrum) of the molecules in the sample can be acquired. Hereinafter, this output signal is called a CARS signal. The acquisition of a CARS signal is described in Non Patent Literature 3 in details.

On the other hand, the Stokes light generates reflected light in accordance with the spatial distribution of the index of refraction of the sample in the vicinity of the light-collecting position. This reflected light travels coaxially with and in the opposite direction of the optical path of the Stokes light incident on the sample, passes through the dichroic mirror 108, and then is reflected at the non-polarizing beam splitter 107. (Although the transmitted component also is generated, this is ignored here). Then, the reference light is reflected at the mirror 114 to travel along the optical path in the opposite direction, and is transmitted through the beam splitter 107 (although there is a reflected component, this is ignored here). Then, the reference light and the reflected light of the Stokes light from the sample are made coaxial to be interfering light, which is then incident on a spectroscope 115, where the wavelength spectrum is output as a detected signal. This detected signal undergoes Fourier transform, which is then output in the form of a signal representing the spatial distribution of index of refraction in the depth of focus within the area irradiated with the Stokes light of the sample. This signal is equal to a signal obtained by a measurement scheme known as Optical Coherence Tomography (OCT), and this is called an OCT signal hereinafter. The measurement principle of OCT is described in Non Patent Literature 6, for example.

Herein the computer 11 sends a signal to shift the position of a piezo stage 12 on which the sample 110 is mounted, and acquires the CARS signal and the OCT signal generated from each position of the sample. Repeatedly acquired OCT signals and CARS signals in this way are sent to the computer 11, which are combined with positional information on the sample and then converted into image data, and an image is displayed on a monitor 13. At this time, an image of the spatial distribution of index of refraction of the sample is displayed based on a series of OCT signals, and an image of the spatial distribution of each molecular species of the sample is displayed based on a series of CARS signals. The direction of scanning the sample, i.e., the piezo-stage 12 may be any of one-dimensional, two-dimensional and three-dimensional, depending on information to be acquired. For instance, when scanning is performed three-dimensionally, three-dimensional spatial distribution images of each molecular species and index of refraction can be obtained. This image data can be dealt with as quantitative data, and so numerical data as the source of the images is stored in the computer 11.

Figure 2:
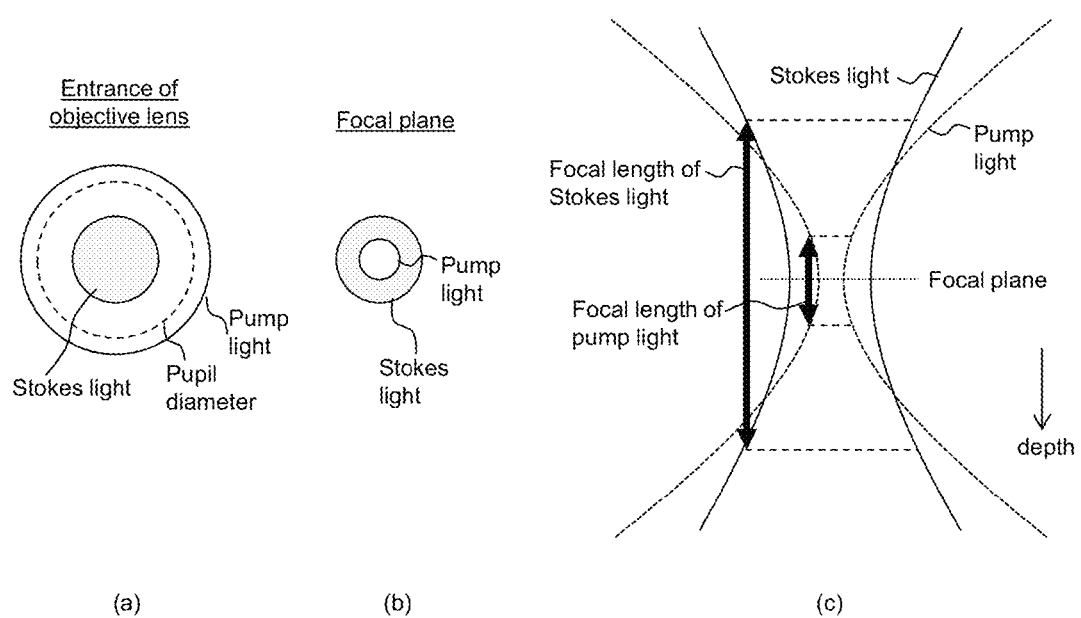
FIG. 2 illustrates beam shapes of pump light and Stokes light.

Referring now to FIG. 2, beam diameters of the pump light and the Stokes light are described below. In the present embodiment, the beam diameter of the pump light is set larger than the beam diameter of the Stokes light, and the beam diameter of the pump light is set at the same degree as the effective diameter of the objective lens 109 or more. That is, as illustrated in FIG. 2(a), the amount of light of the pump light is distributed all over the effective diameter of the objective lens 109, and the amount of light of the Stokes light is distributed in the vicinity of the center in the effective diameter only. At this time, the pump light is collected to be about a spot size that is a diffraction limit determined by the numerical aperture of the objective lens 109. On the other hand, the Stokes light is equal to the collection with a lens having a substantially smaller numerical aperture. Since the spot size on the focal plane (light-collecting position) is inversely proportional to the numerical aperture, the spot size of the pump light is smaller than the spot size of the Stokes light as illustrated in FIG. 2(b). Then since the depth of focus is inversely proportional to the square of the numerical aperture, the depth of focus of the Stokes light is longer than the depth of focus of the pump light as illustrated in FIG. 2(c). Further, the intensity of the CARS light is proportional to the square of the intensity of the pump light, and is proportional to the intensity of the Stokes light. That is, the CARS light is emitted only from the region where the pump light and the Stokes light are overlapped. Since both of the pump light and the Stokes light are collected typically with a high numerical aperture, the region in the depth of focus of the pump light and the region in the depth of focus of the Stokes light roughly agree, and the CARS light is emitted only from these regions. In the present embodiment as well, the CARS light is emitted only from a narrow region of the same degree, and so one-dimensional, two-dimensional or three-dimensional quantitative spatial distribution of molecular species can be obtained by scanning the focus position using the piezo stage 12. Herein, since the Stokes light is extended more widely on the focal plane than the pump light, the energy density in the depth of focus of the Stokes light is smaller than that collected with a numerical aperture equal to the pump light, and the generation efficiency of the CARS signals is accordingly restricted. However, the generation efficiency of the CARS light is proportional to the square of the intensity of the pump light, and so CARS light of sufficient intensity can be generated by entering the pump light of sufficient intensity. Meanwhile, the reflected light of the Stokes light is used for the measurement of the spatial distribution of index of refraction in the depth of focus (setting the position in the optical-axis direction as a variable) as stated above. Herein, the depth of focus of the Stokes light increases by the amount corresponding to a decreased numerical aperture of the Stokes light set, meaning that a smaller numerical aperture set enables the measurement of the spatial distribution of index of refraction in a larger range. Conversely, in order to generate CARS light effectively, the numerical aperture of the pump light is set at around 1. If the Stokes light is collected with the numerical aperture of the same degree, then the depth of focus will be at the same degree as the wavelength of the Stokes light, and so the range of the index of refraction (in the optical-axis direction) acquired from the measurement once becomes extremely narrow, and additionally the amount of the reflected light becomes extremely small due to a small depth of focus, resulting in difficulty to measure the spatial distribution of index of refraction. In this way, the numerical aperture of the Stokes light is set smaller than that of the pump light, whereby the spatial distribution of the index of refraction can be measured effectively, and the CARS signal also can be acquired with sufficient resolution and sensitivity.

The present embodiment enables acquisition of the spatial distribution of molecular species and the spatial distribution of index of refraction of a sample such as cells as stated above. Such an image may be acquired continuously, whereby a change over time of cells or the like can be acquired as a time-lapse image. In this case, a plurality of pieces of image data is stored in the computer 11, which are displayed in the form of moving images or frame-by-frame advance images on the monitor 13 as a change over time. Images on such a change over time may be collected as one piece of data, and may be stored in the computer 11.

In the present embodiment, the focal length of the collimate lens 105 is adjusted so as to set the beam diameter of the Stokes light smaller than the beam diameter of the pump light and so achieve a relatively small numerical aperture. The method of decreasing the numerical aperture substantially is not limited to this, and for example, an opening limiting may be disposed immediately after the collimate lens 105, whereby the beam diameter is decreased to the size of the opening to implement a small numerical aperture substantially. The definition of the beam diameter may be a full width at half maximum, for example, or when the pump light and the Stokes light are close to a Gaussian beam, this may be a width of e^-2 of the peak value by fitting using a Gauss function. In any case, the pump light and the Stokes light should have the same definition.

Figure 13:
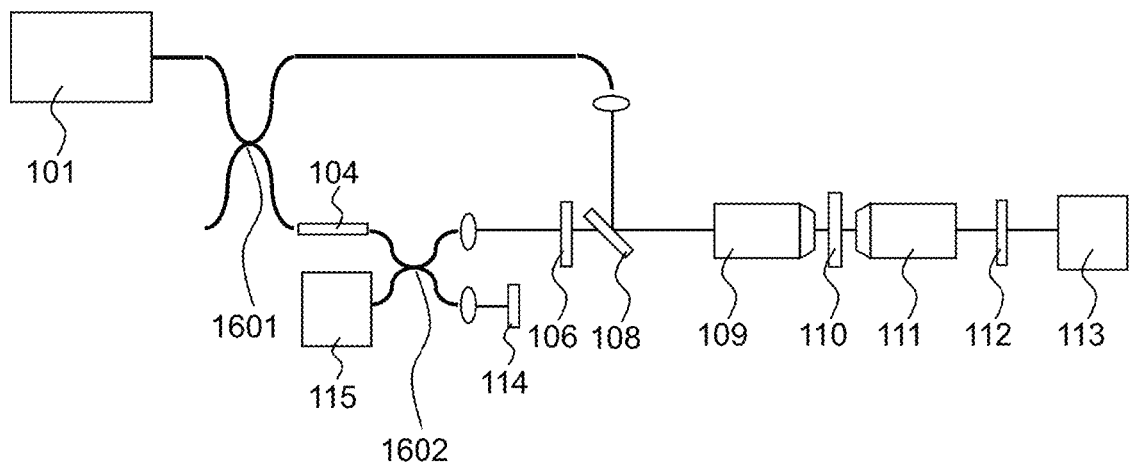
FIG. 13 illustrates the configuration where a part of the configuration of FIG. 1 is replaced with an optical fiber.
Figure 14:
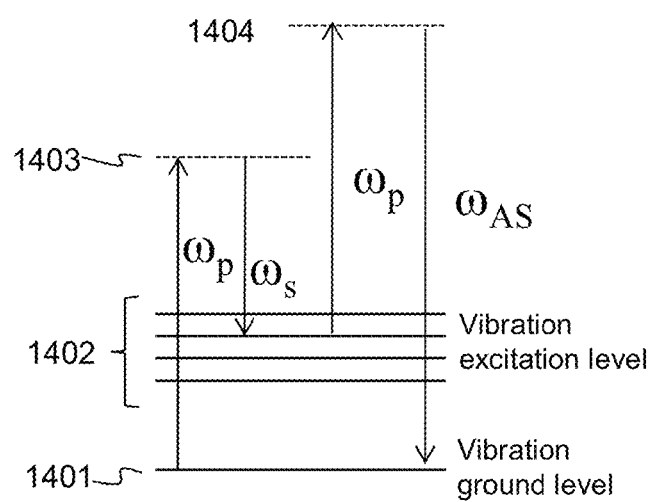
FIG. 14 is an energy diagram representing the generation of resonant CARS light.
Figure 15:
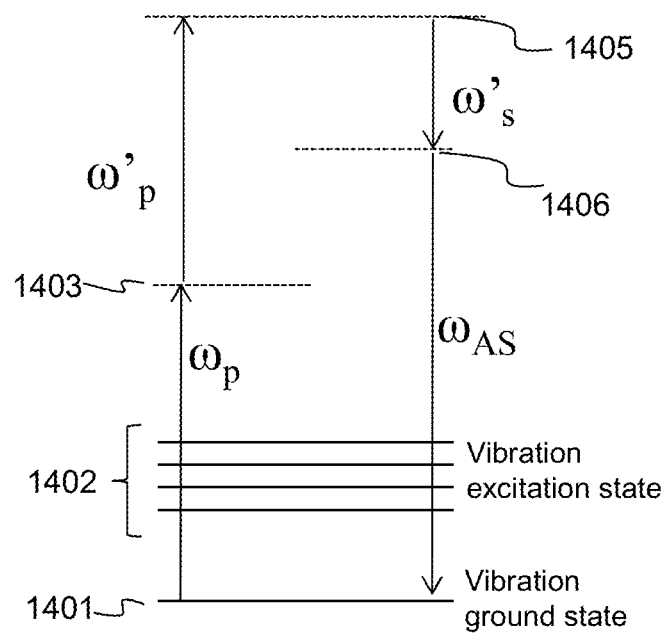
FIG. 15 is an energy diagram representing the generation of non-resonant CARS light.
Figure 16:
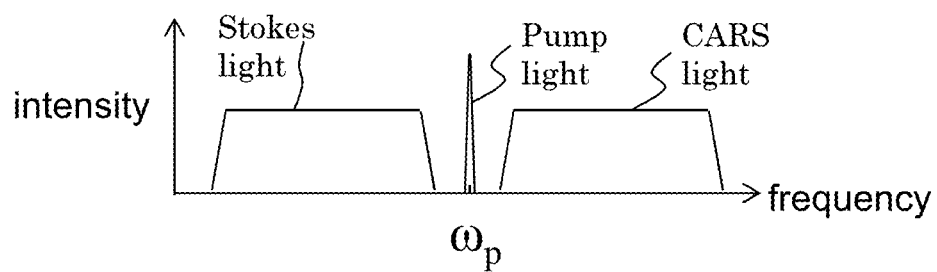
FIG. 16 represents a relationship of frequencies among pump light, Stokes light and CARS light.

The present embodiment is configured so that the optical system is disposed in the free space except for the photonic crystal fiber, and a part of the optical system may be replaced with an optical fiber in one form of the implementation. For instance, FIG. 13 illustrates such an embodiment, in which the function similar to that of FIG. 1 is configured using an optical fiber. In this case, a short-pulse laser light source 101 used has an output that waveguides an optical fiber, and fiber couplers 1601 and 1602 are used instead of the beam splitter 102 and the non-polarizing beam splitter 107, respectively. Then the input/output of light to the photonic crystal fiber 104 is performed by directly jointing with an optical fiber. The same goes for the following embodiments, where a part of the optical system may be replaced with an optical fiber.

In the present embodiment, the photonic crystal fiber is used as a means to generate broadband light, and a highly nonlinear fiber may be used that can generate similar supercontinuum light.

Figure 17:
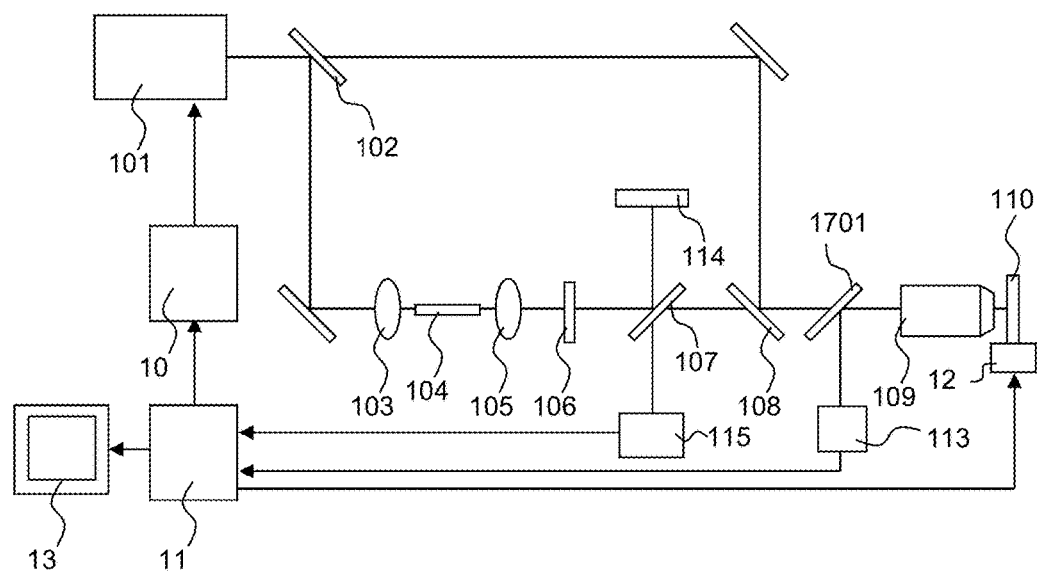
FIG. 17 illustrates a configuration to detect CARS light that is generated in the direction opposite to the light incident on a sample.

The present embodiment is configured as a so-called transmissive structure, in which components are detected as the CARS light in the same traveling direction as the pump light and the Stokes light. Instead, this may be configured as a reflective structure where components emitted in the direction opposite to the pump light and the Stokes light also are present as the CARS light. In this case, as illustrated in FIG. 17, the CARS light generated is made parallel light at the objective lens 109, and then the CARS light only is reflected at a dichroic mirror 1701 and is detected by a spectroscope 113. The dichroic mirror 1701 has a property of transmitting wavelength components of the pump light and the Stokes light, and reflecting a wavelength component of the CARS light. Then, the pump light and the Stokes light from the dichroic mirror 108 are transmitted, the Stokes light reflected at the sample is transmitted, and the CARS light is reflected, so that the CARS signal and the OCT signal can be acquired in this configuration. A non-polarizing beam splitter or the like may be used instead of the dichroic mirror 1701. In this case, although light other than desired wavelength components is incident on the spectroscopes 115 and 113, these spectroscopes separate the wavelength components for detection, whereby unnecessary components can be removed.

Figure 18:
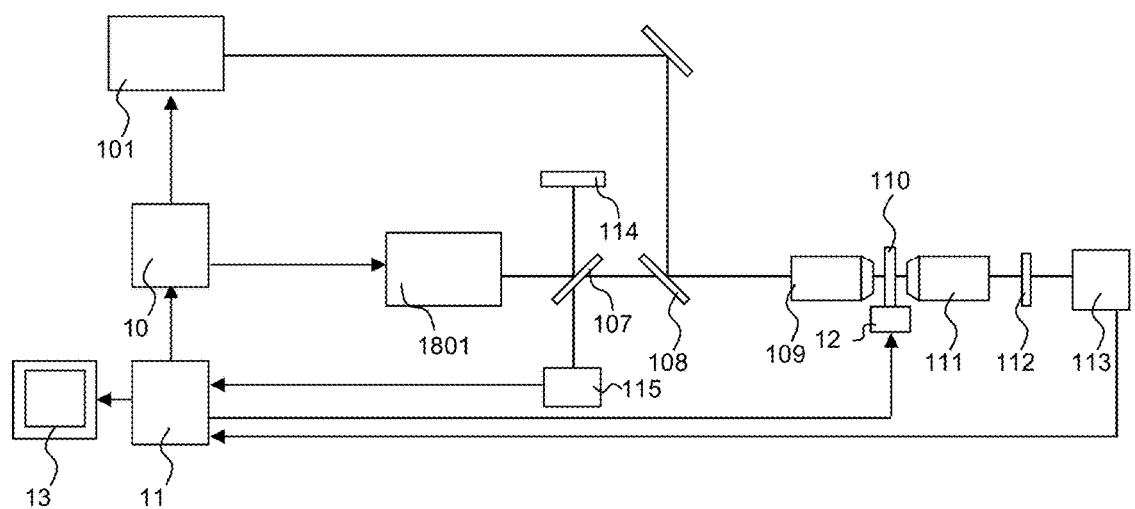
FIG. 18 illustrates a configuration where a broadband laser light source is used as the Stokes light.

In the present embodiment, the supercontinuum light that is generated from a part of the pump light source being incident on the photonic crystal fiber 104 is used as the Stokes light, which is not a limiting example actually. For instance, as illustrated in FIG. 18, the output of a femtosecond laser 1801 may be used. Herein the driver 10 controls so that pulse light-emission of the short-pulse laser light source 101 and the femtosecond laser 1801 occurs at the same time.

Figure 19:
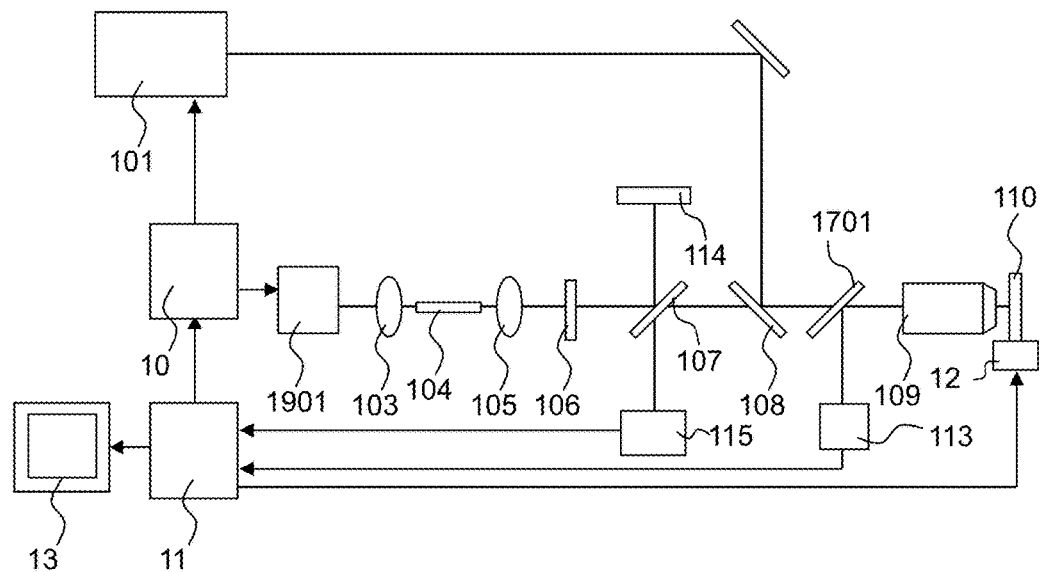
FIG. 19 illustrates a configuration where supercontinuum light is used as the Stokes light, which is obtained by allowing light of a laser light source different from a pump light source to be incident to a photonic crystal fiber.

Light incident on the photonic crystal fiber 104 is not necessarily the same as the pump light source, and as illustrated in FIG. 19, for example, another short-pulse laser light source 1901 may be prepared, and light emitted in synchronization with (at the same timing as) the short-pulse laser light source 101 by the driver 10 may be incident on the photonic crystal fiber 104.

Figure 20:
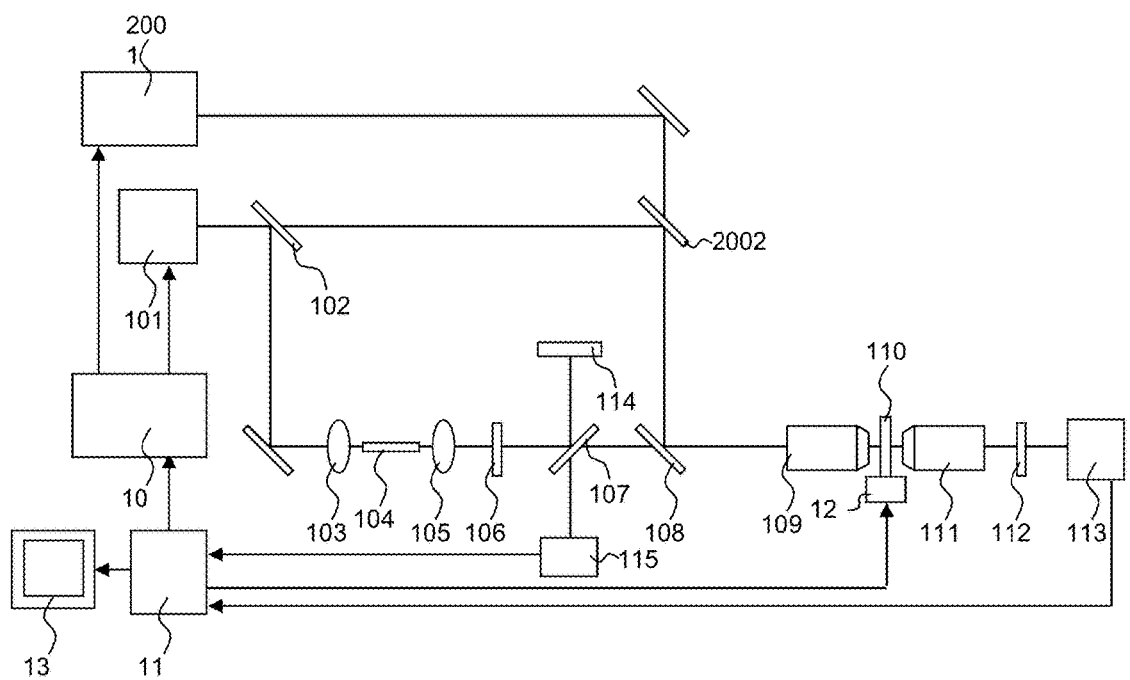
FIG. 20 illustrates a configuration where probe light is used in addition to the pump light and the Stokes light.

In the present embodiment, light incident on the sample includes the pump light and the Stokes light only, and as described at the beginning, the CARS light is obtained typically by letting three types of lights of the pump light, the Stokes light and the probe light in. Then, as illustrated in FIG. 20, a short-pulse laser light source 2001 may be additionally prepared, and light emitted in synchronization with the short-pulse laser light source may be additionally made incident on the sample as the probe light. In this case, the probe light may have any frequency, which is multiplexed with the pump light and the Stokes light by the dichroic mirrors 2002 and 108, and is collected at one point on the sample. Multiplexing may be performed using a non-polarizing beam splitter, instead of the dichroic mirror 2002.

Figure 21:
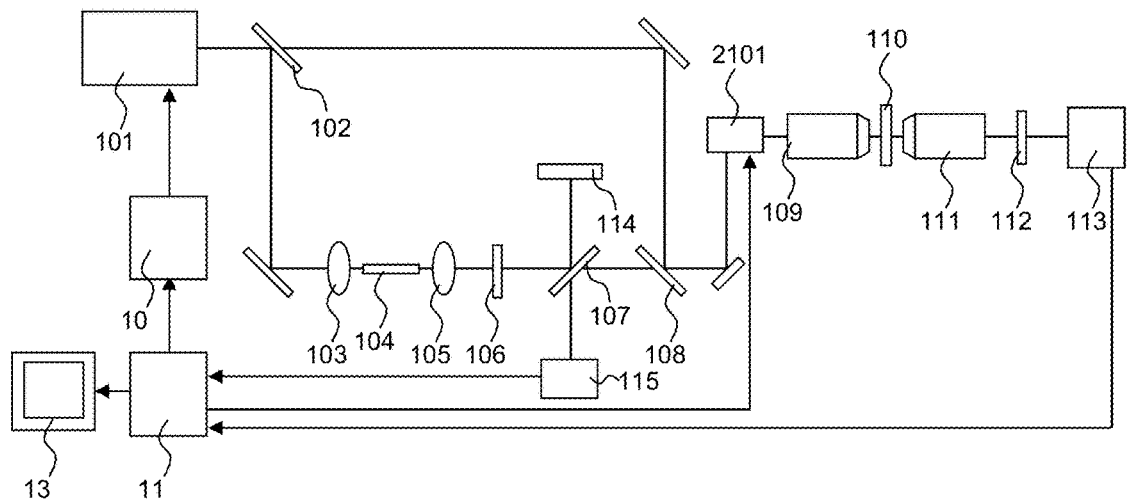
FIG. 21 illustrates a configuration where the light-collecting position of the pump light and the Stokes light is scanned using a galvanic mirror.

In the present embodiment, the piezo stage 12 is used for scanning of the light-collecting position of the pump light and the Stokes light. The method for scanning is not limited to this, and when scanning is performed in the in-plane direction, for example, a galvanic mirror 2101 disposed upstream of the objective lens 109 may be used for scanning as illustrated in FIG. 21. The galvanic mirror is made up of two mirrors, each of which is rotated by external drive control, and as a result the optical-axis directions of the laser lights reflected at the two mirrors can be scanned two-dimensionally. For scanning in the depth direction of a sample, the objective lens 109 may be mounted in the optical-axis direction on a piezo stage or the like for scanning in the depth direction.

[Non Patent Literature 6] M. Wojtkowski et al., "Full range complex spectral optical coherence tomography technique in eye imaging", Optics Letters, Vol. 27, Issue 16, pp. 1415-1417 (2002)

Embodiment 2

Figure 3:
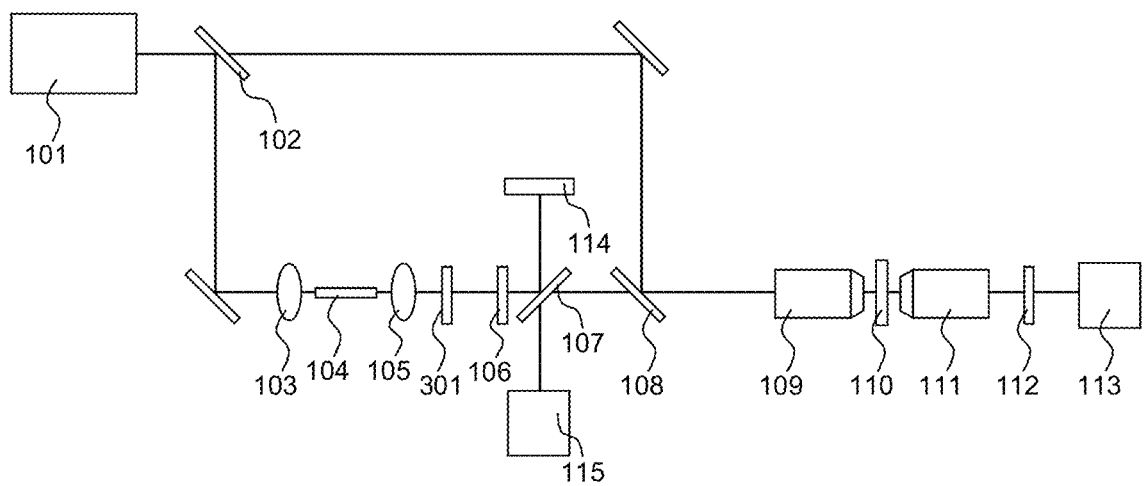
FIG. 3 illustrates an embodiment to switch a beam diameter of the Stokes light.
Figure 4:
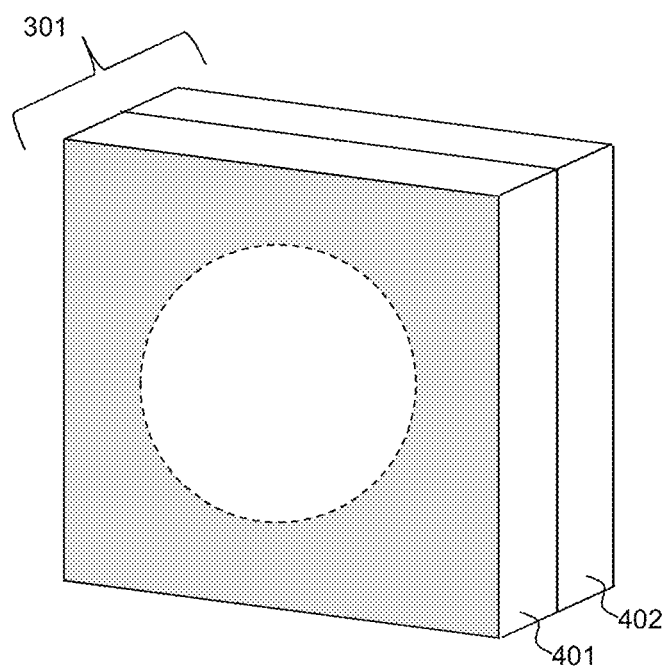
FIG. 4 illustrates a liquid crystal phase modulator in details.
Figure 5:
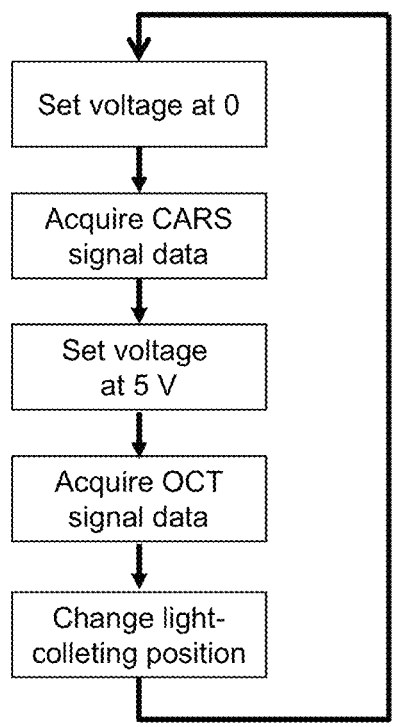
FIG. 5 is a block diagram to acquire data in one embodiment to switch a beam diameter of the Stokes light.

The present embodiment is another embodiment in which the detection of a CARS signal and the detection of an OCT signal in Embodiment 1 are performed in a time-division manner. FIG. 3 illustrates the configuration of the present embodiment. This configuration is different from Embodiment 1 in that a liquid crystal opening element 301 is inserted immediately after the collimate lens 105 in the optical path of the Stokes light. The liquid crystal opening element has a configuration as in FIG. 4 so that a liquid crystal modulation element 401 and a polarizer 402 are integrated. The liquid crystal modulation element 401 enables a selection between a region outside of a predetermined circular opening rotating the polarization of the incident light (let that this is horizontal polarization) by 90 degrees and the region not rotating the polarization, depending on the presence or not of driving voltage. The region inside of the circular opening lets the incident light pass through without changing the polarization irrespective of the driving voltage. The polarizer 402 is to transmit horizontal polarized light and to block vertical polarized light. That is, when voltage driving is not performed (driving voltage is 0 V), incident light passes through as it is, and when voltage driving is performed (let that driving voltage is 5V), light in the circular opening region passes through. That is, the beam diameter of the Stokes light, and accordingly a substantial numerical aperture can be changed depending on the presence or not of driving voltage. In the present embodiment, data is acquired using this element in accordance with the procedure as in FIG. 5. That is, voltage is set at 0 V, and a CARS signal is acquired in the state of a high numerical aperture of the Stokes light. Thereafter, voltage is set at 5 V, and an OCT signal is acquired in the state of a low numerical aperture of the Stokes light. Then similar signal acquisition is repeated while changing a light-collecting position, whereby the spatial distribution of each chemical species by the CARS signal and the spatial distribution of index of refraction by the OCT signal are acquired. According to the present embodiment, the numerical aperture of the Stokes light can be high during acquisition of a CARS signal, and so the CARS signal can be acquired effectively as compared with Embodiment 1.

Figure 6:
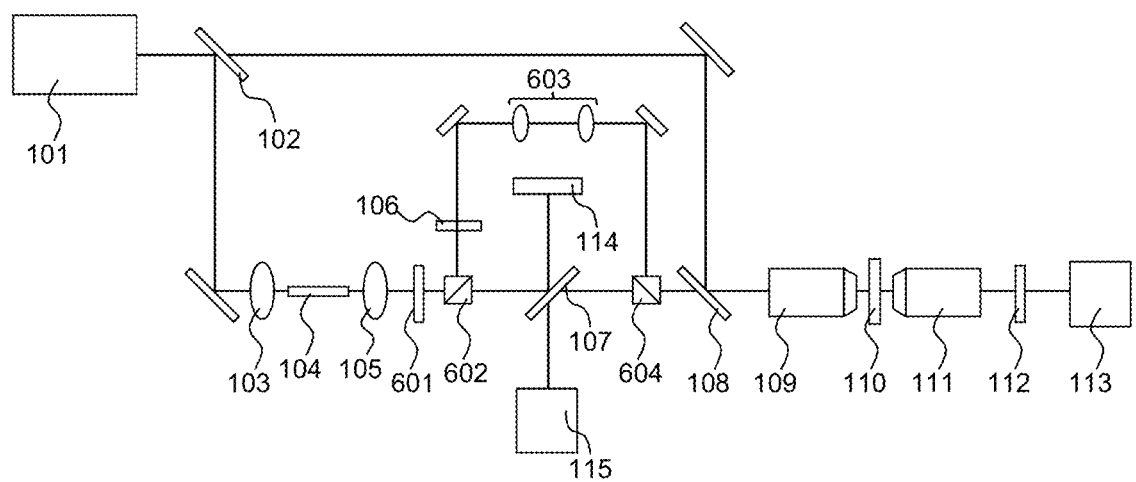
FIG. 6 illustrates another embodiment to switch a beam diameter of the Stokes light.

In the method of the present embodiment, the liquid crystal modulation element 401 is not necessarily required. For instance, the present embodiment can be implemented with the configuration as illustrated in FIG. 6. In this case, the Stokes light passing through the collimate lens 105 then passes through a liquid crystal λ/2 plate 601, and then enters a polarizing beam splitter 602. Herein, the liquid crystal λ/2 plate is an element that does not change the polarization (herein horizontal polarization) of incident light when the driving voltage is 0 V, and rotates the polarization of incident light by 90 degrees (i.e., changing it into vertical polarized light). Since the polarizing beam splitter 602 transmits horizontal polarized light and reflects vertical polarized light, when the driving voltage is 0 V, the Stokes light passes through the polarizing beam splitter 602, and when the driving voltage is 5 V, the Stokes light is reflected at the polarizing beam splitter 602. Transmitted light from the polarizing beam splitter 602 is divided into two by the non-polarizing beam splitter 107 similarly to Embodiment 1, and then passes through a polarizing beam splitter 604 to be applied to a sample 110, and then the reflected light is detected by the spectroscope 115 as an OCT signal. Herein the beam diameter of the Stokes light is set smaller than the effective diameter of the objective lens 109, and so irradiation of the sample is performed with a low numerical aperture similarly to Embodiment 1. Meanwhile, the reflected light from the polarizing beam splitter 602 passes through the long-pass filter 106, and then is expanded in beam diameter by the beam expander 603, which is then reflected by a polarizing beam splitter 604 to be applied to the sample 110. Then the resultant generates CARS light together with the pump light, and this CARS light is then detected by a spectroscope 113 similarly to Embodiment 1. The beam expander 603 expands the beam diameter of the Stokes light to be the same degree of the effective diameter of the objective lens or more, and so is collected at the sample 110 with a high numerical aperture. That is, the liquid crystal λ/2 plate 601 functions substantially similarly to the liquid crystal modulation element 401, and so a CARS signal and an OCT signal can be acquired in accordance with the block diagram of FIG. 5.

Embodiment 3

Figure 7:
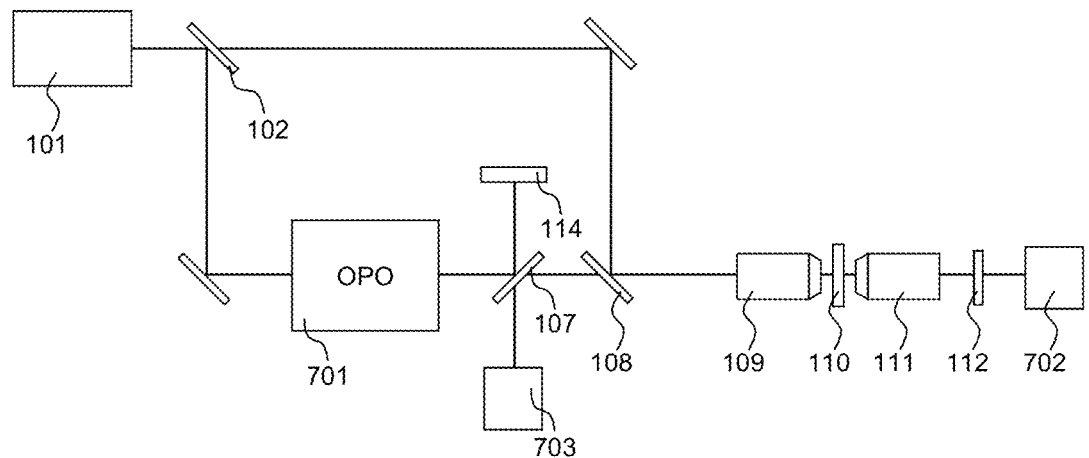
FIG. 7 illustrates an embodiment including a wavelength swept light source.

In the present embodiment, a wavelength swept light source is used as the Stokes light. FIG. 7 illustrates the configuration of the present embodiment. The configuration of the present embodiment is basically the same as Embodiment 1, and is different in that the output of an optical parametric oscillator 701 is used as the Stokes light, and a detector that converts the total amount of light received into an electrical signal detects the CARS light and the Stokes light instead of a spectroscope. The optical parametric oscillator 701 has a function to convert the wavelength of the pump light, and so can tune the wavelength of light output continuously. For data acquisition, wavelength-sweeping is continuously performed, and then data is acquired by associating the output of detectors 702 and 703 at some time relative to the set wavelength with an output signal at some wavelength of the spectroscopes 113 and 115 of Embodiment 1. Such acquisition of a CARS signal and an OCT signal using the wavelength swept light source is described in Non Patent Literature 7 and Non Patent Literature 8, respectively.

[Non Patent Literature 7] S, Begin et al., "Coherent anti-Stokes Raman scattering hyperspectral tissue imaging with a wavelength-swept system", Biomedical Optics Express, Vol. 2, Issue 5, pp. 1296-1306 (2011)

[Non Patent Literature 8] Y. Yasuno et al., "Three-dimensional and high-speed swept-source optical coherence tomography for in vivo investigation of human anterior eye segments", Optics Express, Vol. 13, Issue 26, pp. 10652-10664 (2005)

Embodiment 4

Figure 8:
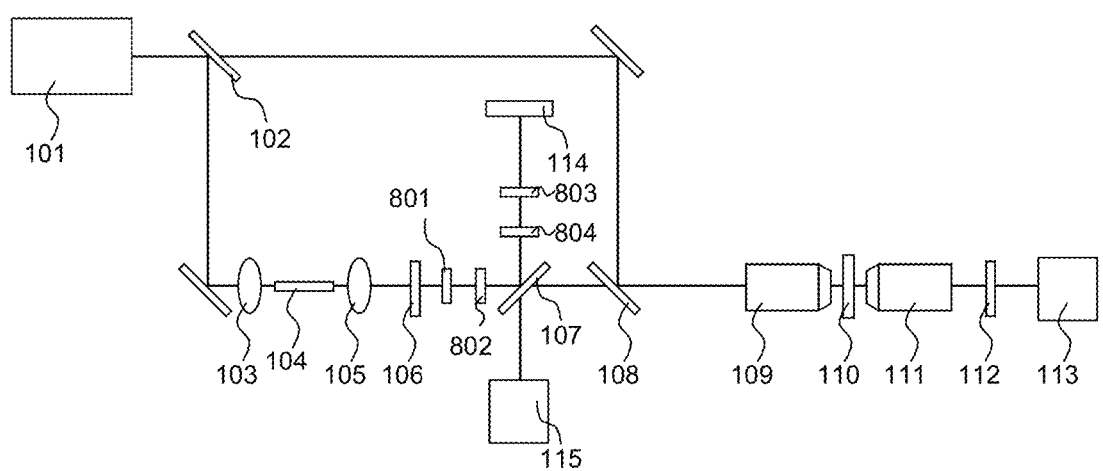
FIG. 8 illustrates an embodiment to acquire information on birefringence from a sample.

The present embodiment is another embodiment, in which the birefringence state of the sample is investigated through OCT detection. FIG. 8 illustrates the configuration of the present embodiment. In the present embodiment, a liquid crystal λ/2 plate 801 and a liquid crystal λ/4 plate 802 are inserted between the collimate lens 105 and the non-polarizing beam splitter 107, and a liquid crystal λ/4 plate 803 and a liquid crystal λ/8 plate 804 are inserted between the non-polarizing beam splitter 107 and the mirror 114. Herein, the combination of driving voltages of the liquid crystal λ/2 plate 801, the liquid crystal λ/4 plate 802, the liquid crystal λ/4 plate 803 and the liquid crystal λ/8 plate 804 enables the polarization state of the reference light and the reflected light of the Stokes light (immediately before multiplexing) to be set at any one of horizontal polarization, vertical polarization, 45-degree linear polarization and right circular polarization. In the present embodiment, measurement is performed in sixteen ways (4×4=16) in total as the combination of these polarization states, and the spatial distribution of birefringence is synthesized through the following operation based on the acquired data:

[Math. 3]
$$M = \begin{pmatrix} M_{00} & M_{01} & M_{02} & M_{03} \\ M_{10} & M_{11} & M_{12} & M_{13} \\ M_{20} & M_{21} & M_{22} & M_{23} \\ M_{30} & M_{31} & M_{32} & M_{33} \end{pmatrix} =$$

$$\frac{1}{2}\begin{pmatrix} I_{HH}+I_{HV}+I_{VH}+I_{VV} & I_{HH}+I_{HV}-I_{VH}-I_{VV} & 2I_{DH}+2I_{DV}-M_{00} & 2I_{RV}+2I_{DV}-M_{00} \\ I_{HH}-I_{HV}+I_{VH}-I_{VV} & I_{HH}-I_{HV}-I_{VH}+I_{VV} & 2I_{DH}-2I_{DV}-M_{10} & 2I_{RH}-2I_{RV}-M_{10} \\ 2I_{HD}+2I_{VD}-M_{00} & 2I_{HD}-2I_{VD}-M_{01} & 4I_{DD}-2I_{DH}-2I_{DV}-M_{20} & 4I_{RD}-2I_{RH}-2I_{RV}-M_{20} \\ 2I_{HR}+2I_{VR}-M_{00} & 2I_{HR}-2I_{VR}-M_{01} & 4I_{DR}-2I_{DH}-2I_{DV}-M_{30} & 4I_{RR}-2I_{RH}-2I_{RV}-M_{30} \end{pmatrix}$$

where H, V, D and R denotes horizontal polarization, vertical polarization, 45-degree linear polarization and right circular polarization, respectively, and the first suffix represents the polarization state of the reference light and the second suffix represents the polarization state of the reflected light of the Stokes light. For instance, in the case of IHV, this is the output of an OCT signal when the polarization state of the reference light is H and the polarization state of the Stokes light is V. Patent Literature 1 describes the principle of this measurement in details. The matrix represented in [Math. 3] is known as Mueller matrix, and this matrix itself represents birefringence quantitatively. The measurement is actually performed through the OCT measurement in sixteen ways as stated above in the state where the pump light and the Stokes light are set at a predetermined light-collecting position. For a CARS signal, detection is performed only when the Stokes light is in the state of horizontal polarization (the same polarization state as the pump light) (combinations in four ways in total), and the sum of these signals is used as the CARS signal. Then after finishing the measurement of these combinations in sixteen ways, then similar measurement is repeated while changing the light-collecting position. In this way, the spatial distribution of birefringence by the OCT signal and the spatial distribution of molecular species by the CARS signal can be acquired.

[Patent Literature 1] JP 4045140 B

Embodiment 5

Figure 9:
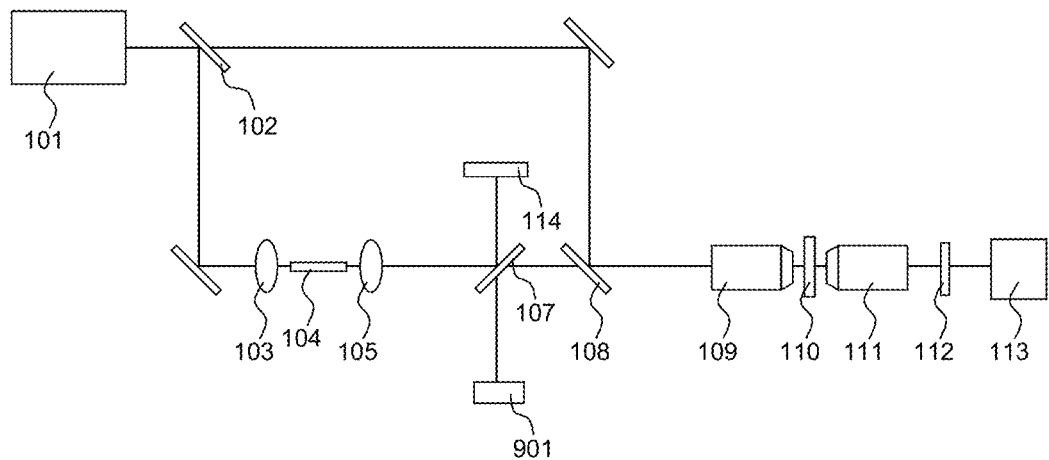
FIG. 9 illustrates an embodiment to detect reflected light of the Stokes light from the sample without dispersion.
Figure 10:
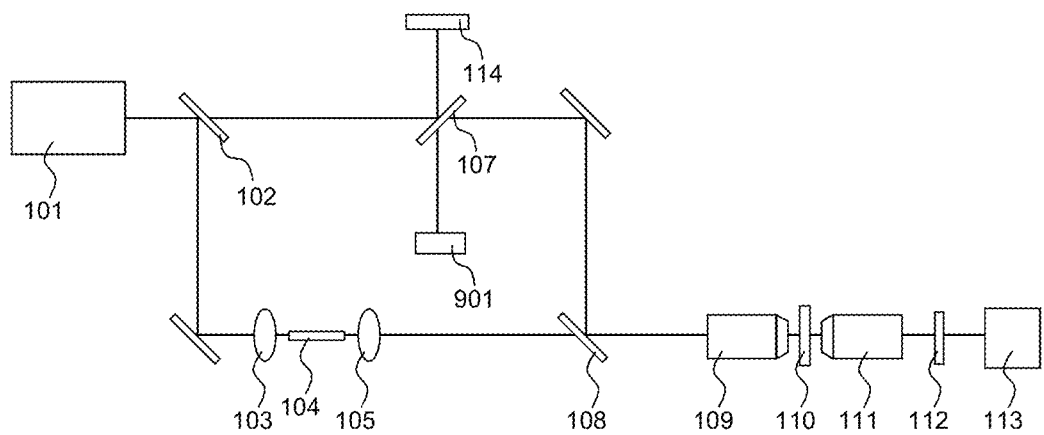
FIG. 10 illustrates an embodiment to detect reflected light of the pump light from the sample without dispersion.
Figure 11:
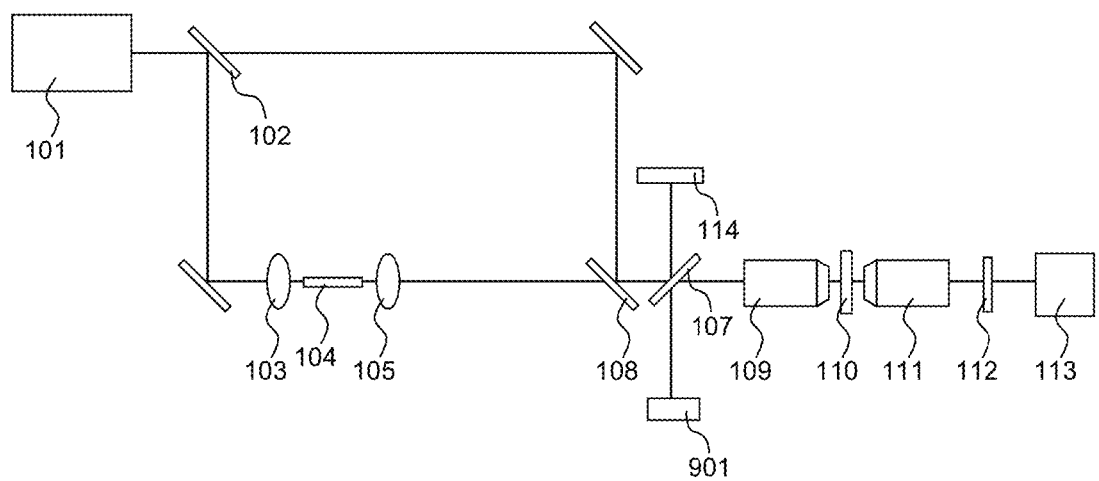
FIG. 11 illustrates an embodiment to detect reflected light of a multiplexed light flux of the pump light and the Stokes light from the sample without dispersion.

The present embodiment is another embodiment, in which reflected light of light applied to a sample is detected without dispersion. FIG. 9 illustrates the configuration of the present embodiment. Basically the present embodiment is different from Embodiment 1 in that the numerical aperture of the Stokes light is set at the same degree of the pump light, and in that the reflected light of the Stokes light from the sample is detected by not a spectroscope but a detector 901 that detects the total amount of light. In this case, the numerical aperture of the Stokes light is high, and the area in the depth of focus is accordingly narrowed as stated above, and so the amount of reflected light is small. However, reflected light from the interface between different substances (e.g., cell membrane) can have sufficient intensity in such a configuration as well, and so the reflected light can be acquired. That is, the spatial distribution of molecular species by a CARS signal as well as the spatial distribution at the interface of the sample to be observed (e.g., the contour of a cell) can be visualized by scanning the light-collecting position. For such detection of the reflected light, a broadband light source is not necessarily required, and the pump light is divided into two by the non-polarizing beam splitter 107 as in FIG. 10, for example, and the reflected light of the pump light from the sample may be allowed to interfere with the reflected light from the mirror 114 for detection, whereby a similar signal can be acquired. Alternatively, as in FIG. 11, a light flux that is obtained by multiplexing the pump light and the Stokes light may be used for similar detection. Broadband Stokes light is not necessarily required, and the parametric oscillator in Embodiment 3 may be used instead of the photonic crystal fiber 104, for example, which then may be used with a fixed wavelength without performing wavelength-sweeping.

Embodiment 6

Figure 12:
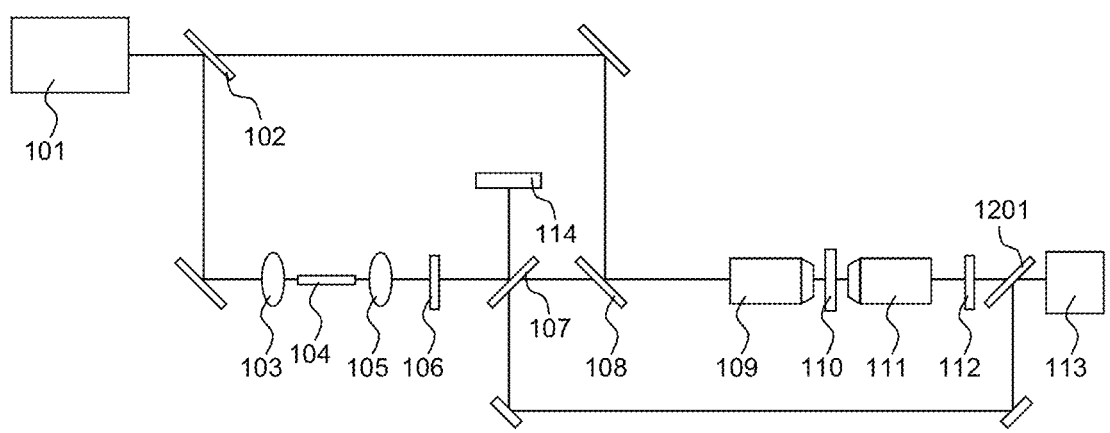
FIG. 12 illustrates an embodiment to acquire a CARS signal and an OCT signal with one spectroscope.

The present embodiment is configured to include a common spectroscope instead of the spectroscopes 113 and 115 of Embodiment 1. FIG. 12 illustrates the configuration of the present embodiment. In the case of the present embodiment, interfering light generated similarly to Embodiment 1 is multiplexed with the CARS light at a dichroic mirror 1201, which is then incident on the spectroscope 113. Since the spectra of the CARS light and the interfering light (Stokes light) do not overlap basically, a CARS signal can be obtained at a predetermined wavelength area of the output of the spectroscope, and an OCT signal can be acquired at another wavelength area.

Embodiment 7

Figure 22:
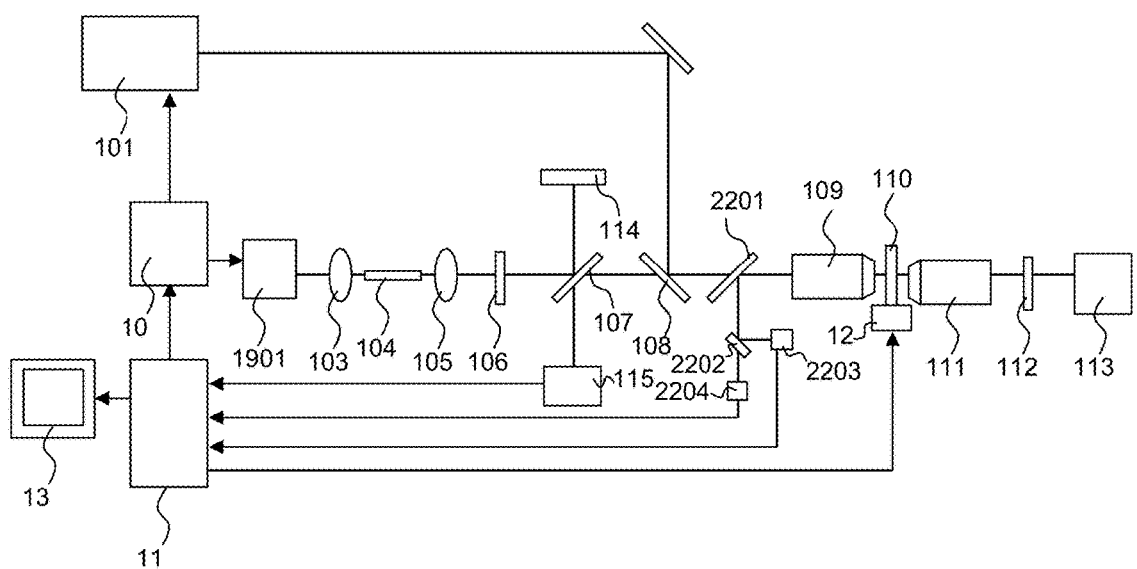
FIG. 22 illustrates an embodiment to detect SHG and two-photon fluorescence in addition to a CARS signal and an OCT signal.

The present embodiment is configured to acquire SHG and two-photon fluorescence in addition to a CARS signal and an OCT signal at the same time. FIG. 22 illustrates the configuration of the present embodiment. In the present embodiment, when pump light is collected at a sample for irradiation, SHG and two-photon fluorescence occur in addition to CARS light. In the present embodiment, a reflected component of SHG and two-photon fluorescence (i.e., a light-emission component that travels in the direction opposite to the pump light) is made parallel at the objective lens 109, and these light fluxes are reflected at a dichroic mirror 2201 and are incident on a dichroic mirror 2202. The dichroic mirror 2202 has a property of reflecting the wavelength component of SHG and transmitting the wavelength component of two-photon fluorescence, and so SHG and two-photon fluorescence can be separated. The light fluxes of the separated SHG and two-photon fluorescence are detected by different detectors 2203 and 2204, respectively. In this way, similarly to Embodiment 1, a CARS microscope image, an OCT image, a SHG image and a two-photon fluorescence image can be acquired by scanning the light-collecting position at the sample.

Figure 23:
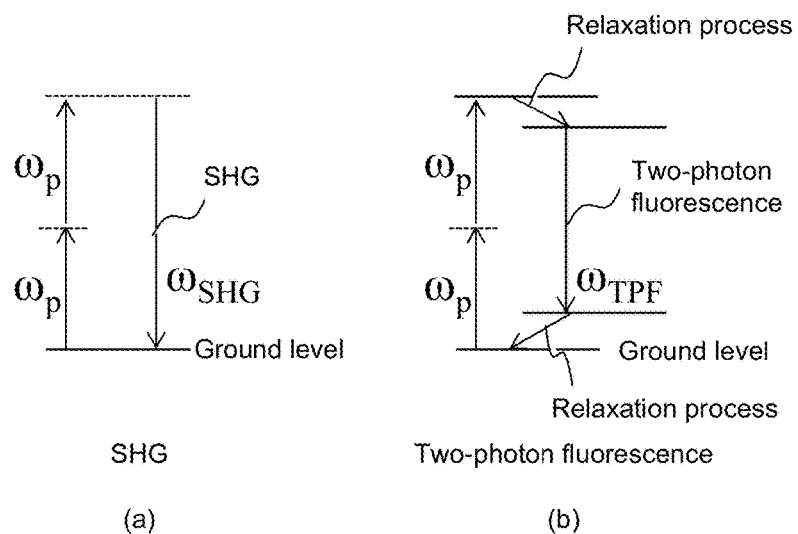
FIG. 23 is an energy diagram of SHG and two-photon fluorescence.

FIG. 23 is an energy diagram of SHG and two-photon fluorescence. SHG is the process where incident light generates light with a double frequency (i.e., the wavelength is half) not via a real state (i.e., without involving absorption). Two-photon fluorescence is the process where incident light is absorbed at the two-photon absorption process, and fluorescence is generated after relaxation process. The fluorescence has the frequency that is slightly smaller than twice the frequency of the incident light. They emit light selectively in accordance with the structure of a sample and the molecular species, and so can be used for observation of a biological sample. These images are acquired together with a CARS signal and an OCT signal, whereby more information can be acquired from the sample (see Non Patent Literature 1 and Non Patent Literature 2 for details of SHG and two-photon fluorescence, respectively).

Figure 24:
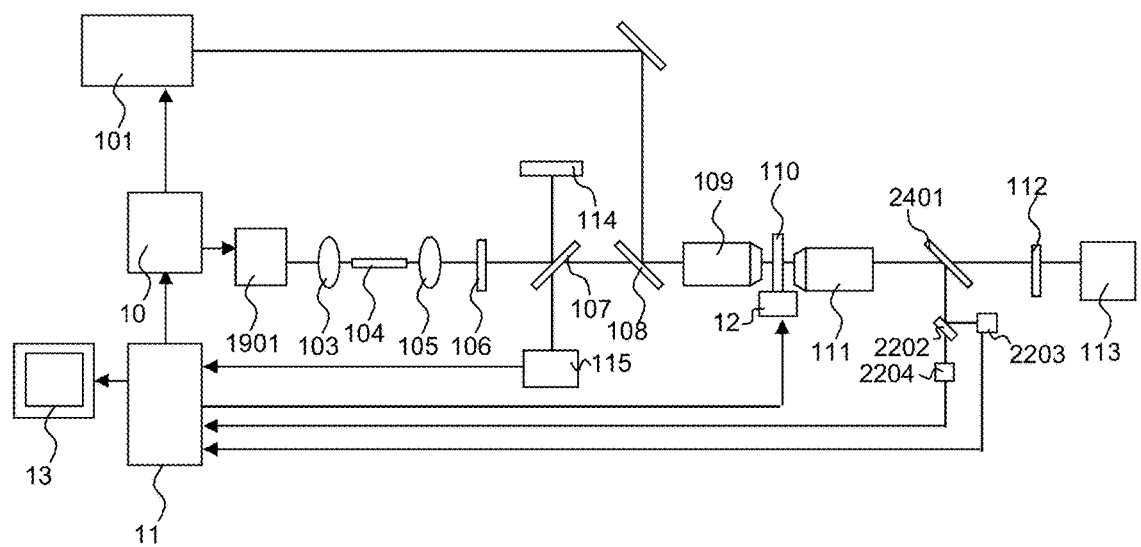
FIG. 24 illustrates a configuration to detect transmitted components of SHG and two-photon fluorescence.

The present embodiment acquires both images for SHG and two-photon fluorescence, and one of them may be omitted. The present embodiment has a reflective configuration for both of the SHG and the two-photon fluorescence, and they include a component (transmitted component) emitted in the same direction as that of the pump light similarly to a CARS signal. Then a dichroic mirror 2401 may be disposed downstream of the objective lens 111 as in the configuration of FIG. 24 to detect transmitted components of the SHG and the two-photon fluorescence. In this case, the dichroic mirror 2401 has a property of transmitting the wavelength component of a CARS signal and reflecting the wavelength components of the SHG and the two-photon fluorescence.

REFERENCE SIGNS LIST

101 Short-pulse laser light source
102 Beam splitter
103 Collecting lens

104 Photonic crystal fiber
105 Collimate lens
106 Long-pass filter
107 Non-polarizing beam splitter
108 Dichroic mirror
109 Objective lens
110 Sample
111 Condenser lens
112 Short-pass filter
113 Spectroscope
114 Mirror
115 Spectroscope
301 Liquid crystal opening element
401 Liquid crystal modulation element
402 Polarizer
601 Liquid crystal λ/2 plate
602 Polarizing beam splitter
603 Beam expander
604 Polarizing beam splitter
701 Optical parametric oscillator
702 Detector
703 Detector
801 Liquid crystal λ/2 plate
802 Liquid crystal λ/4 plate
803 Liquid crystal λ/4 plate
804 Liquid crystal λ/8 plate
901 Detector
1201 Dichroic mirror
1601 Fiber coupler
1602 Fiber coupler
1701 Dichroic mirror
1801 Femtosecond laser
1901 Short-pulse laser light source
2001 Short-pulse laser light source
2002 Dichroic mirror
2101 Galvanic mirror
2201 Dichroic mirror
2202 Dichroic mirror
2203 Detector
2204 Detector
2401 Dichroic mirror

The invention claimed is:

1. A Coherent anti-Stokes Raman Scattering (CARS) microscope, comprising:
   a light source;
   a first light beam splitter that divides a light flux of output light from the light source into a first pump light flux and a second pump light flux;
   a Stokes light source that receives the second pump light flux as an input and outputs a Stokes light flux;
   a mirror that multiplexes the first pump light flux and the Stokes light flux to generate a multiplexed light flux;
   a first lens that collects the multiplexed light flux in a sample;
   a first detector that detects CARS light generated from the sample, the CARS light having a wavelength different from the multiplexed light flux;
   a second lens that guides the CARS light to the first detector;
   a second light beam splitter that lets at least one of the first pump light flux and the Stokes light flux partially branch as a reference light flux while maintaining a wavelength thereof;
   a multiplexing part that multiplexes a light flux from the sample and the reference light flux to generate interfering light; and
   a second detector that detects the interfering light at a same time that the first detector detects the CARS light.

2. The CARS microscope according to claim 1, wherein the Stokes light source makes a wavelength of the Stokes light flux variable continuously.

3. The CARS microscope according to claim 2, wherein the reference light flux and the light flux from the sample each includes Stokes light.

4. The CARS microscope according to claim 3, wherein the Stokes light flux output by the Stokes light source has a light-flux diameter that is smaller than a light-flux diameter of the multiplexed light flux generated by the mirror.

5. The CARS microscope according to claim 3, further comprising:
   a light-flux lens that makes a light-flux diameter of the Stokes light variable.

6. The CARS microscope according to claim 3, further comprising:
   one spectroscope as the first detector and the second detector.

7. The CARS microscope according to claim 1, wherein the Stokes light source generates the Stokes light flux, and
   a wavelength of the Stokes light flux has a broader bandwidth than a wavelength of the second pump light flux.

8. The CARS microscope according to claim 7, wherein the reference light flux and the light flux from the sample each includes Stokes light.

9. The CARS microscope according to claim 8, wherein the Stokes light flux output by the Stokes light source has a light-flux diameter that is smaller than a light-flux diameter of the multiplexed light flux generated by the mirror.

10. The CARS microscope according to claim 8, further comprising:
    a light-flux lens that makes a light-flux diameter of the Stokes light variable.

11. The CARS microscope according to claim 8, further comprising:
    one spectroscope as the CARS light detector and the interfering-light detector.

12. The CARS microscope according to claim 1, further comprising:
    a first polarized-light conversion part that makes polarized light of the reference light arbitrarily variable; and
    a second polarized-light conversion part that makes polarized light of the Stokes light arbitrarily variable.

13. The CARS microscope according to claim 1, further comprising:
    at least one of a third detector that detects second-harmonic generation (SHG) and a fourth detector that detects two-photon fluorescence, the SHG and the two-photon fluorescence being generated from the sample irradiated with a pump light flux.

14. The CARS microscope according to claim 1, further comprising:
    one non-polarizing beam splitter as the second light beam splitter and the multiplexing part.

15. The CARS microscope according to claim 1, wherein the Stokes light flux has a numerical aperture that is a substantially same as a numerical aperture of the pump light multiplexed by the first mirror.

16. A Coherent anti-Stokes Raman Scattering (CARS) microscope, comprising:
    a pump light source that generates pump light;
    a Stokes light source that generates Stokes light;
    a mirror that multiplexes the pump light and the Stokes light for irradiation of a sample;

a CARS light detector that detects CARS light generated from the sample;
a beam splitter that branches a part of the pump light or the Stokes light to generate reference light while maintaining a wavelength thereof;
a multiplexing part that multiplexes the reference light and light from the sample to generate interfering light; and
an interfering-light detector that detects the interfering light at a same time that the CARS light detector detects the CARS light.

17. The CARS microscope according to claim 16, wherein the CARS light and the interfering light are detected in a time-division manner.

* * * * *